United States Patent [19]

Van den Engh et al.

[11] Patent Number: 5,643,796
[45] Date of Patent: Jul. 1, 1997

[54] SYSTEM FOR SENSING DROPLET FORMATION TIME DELAY IN A FLOW CYTOMETER

[75] Inventors: Ger Van den Engh; Richard J. Esposito, both of Seattle, Wash.

[73] Assignee: University of Washington, Seattle, Wash.

[21] Appl. No.: 323,358

[22] Filed: Oct. 14, 1994

[51] Int. Cl.⁶ ................................................. G01N 35/00
[52] U.S. Cl. ...................... 436/50; 436/43; 436/164; 422/68.1; 422/105; 435/3; 435/286.1; 435/286.2; 435/286.4; 209/3.2; 209/4; 209/571; 209/576; 209/127.4; 250/461.2; 361/226
[58] Field of Search ................... 436/164, 43, 50, 43663; 209/3.1–3.2, 4, 571, 576–577, 127.4; 356/72, 73; 250/461.2; 422/68.1, 82.05, 105; 435/3, 1, 289, 291; 361/226

[56] References Cited

U.S. PATENT DOCUMENTS

| | | | |
|---|---|---|---|
| 3,299,354 | 1/1967 | Hogg | 324/71 |
| 3,661,460 | 5/1972 | Elking et al. | 356/36 |
| 3,810,010 | 5/1974 | Thom | 324/71 |
| 3,973,196 | 8/1976 | Hogg | 324/71 |
| 4,014,611 | 3/1977 | Simpson et al. | 356/72 |
| 4,070,617 | 1/1978 | Kachel et al. | 324/71 |
| 4,162,282 | 7/1979 | Fulwyler et al. | 264/9 |
| 4,230,558 | 10/1980 | Fulwyler | 209/3.1 |
| 4,302,166 | 11/1981 | Fulwyler et al. | 425/6 |
| 4,317,520 | 3/1982 | Lombardo et al. | 209/3.1 |
| 4,318,480 | 3/1982 | Lombardo et al. | 209/3.1 |
| 4,318,481 | 3/1982 | Lombardo et al. | 209/3.1 |
| 4,318,482 | 3/1982 | Barry et al. | 209/431 |
| 4,318,483 | 3/1982 | Lombardo et al. | 209/3.1 |
| 4,325,483 | 4/1982 | Lombardo et al. | 209/3.1 |
| 4,361,400 | 11/1982 | Gray et al. | 356/23 |
| 4,395,676 | 7/1983 | Hollinger et al. | 324/71.4 |
| 4,487,320 | 12/1984 | Auer | 209/3.1 |
| 4,631,483 | 12/1986 | Proni et al. | 324/71.4 |
| 4,673,288 | 6/1987 | Thomas et al. | 356/72 |
| 4,691,829 | 9/1987 | Auer | 209/3.1 |
| 4,818,103 | 4/1989 | Thomas et al. | 356/72 |
| 4,845,025 | 7/1989 | Lary et al. | 435/2 |
| 4,981,580 | 1/1991 | Auer | 209/3.1 |
| 4,983,038 | 1/1991 | Ohki et al. | 356/246 |
| 5,005,981 | 4/1991 | Schulte et al. | 366/219 |
| 5,007,732 | 4/1991 | Ohki et al. | 356/73 |
| 5,159,403 | 10/1992 | Kosaka | 356/243 |
| 5,167,926 | 12/1992 | Kimura et al. | 422/67 |
| 5,182,617 | 1/1993 | Yoneyama et al. | 356/440 |
| 5,215,376 | 6/1993 | Schulte et al. | 366/348 |
| 5,259,593 | 11/1993 | Orme et al. | 266/78 |
| 5,260,764 | 11/1993 | Fukuda et al. | 356/73 |

FOREIGN PATENT DOCUMENTS

| | | |
|---|---|---|
| 2024535 | 1/1990 | Japan . |
| 4126066 | 4/1992 | Japan . |
| 4126081 | 4/1992 | Japan . |

OTHER PUBLICATIONS

Flow Cytometry and Cell Sorting, A. Radbruch (Ed.), "Operation of a Flow Cytometer" by Göttlinger et al., 1992, pp. 7–23.

Flow Cytometry: Instrumentation and Data Analysis, Van Dilla et al. (Eds.), "Overview of Flow Cytometry: Instrumentation and Data Analysis" by Martin Van Dilla, 1985, pp. 1–8.

Flow Cytometry: Instrumentation and Data Analysis, Van Dilla et al. (Eds.), "Flow Chambers and Sample Handling," by Pinkel et al., 1985, pp. 77–126.

Flow Cytometry and Sorting (1st Edition), Melamed, Mullaney, Mendelson, et al., John Wiley and Sons, 1979, pp. 3–9.

Primary Examiner—James C. Housel
Assistant Examiner—Rachel Heather Freed
Attorney, Agent, or Firm—Luke Santangelo

[57] ABSTRACT

A droplet flow cytometer system which includes a system to optimize the droplet formation time delay based on conditions actually experienced includes an automatic droplet sampler which rapidly moves a plurality of containers stepwise through the droplet stream while simultaneously adjusting the droplet time delay. Through the system sampling of an actual substance to be processed can be used to minimize the effect of the substances variations or the determination of which time delay is optimal. Analysis such as cell counting and the like may be conducted manually or automatically and input to a time delay adjustment which may then act with analysis equipment to revise the time delay estimate actually applied during processing. The automatic sampler can be controlled through a microprocessor and appropriate programming to bracket an initial droplet formation time delay estimate. When maximization counts through volume, weight, or other types of analysis exists in the containers, the increment may then be reduced for a more accurate ultimate setting. This may be accomplished while actually processing the sample without interruption.

17 Claims, 2 Drawing Sheets

SYSTEM FOR SENSING DROPLET FORMATION TIME DELAY IN A FLOW CYTOMETER

BACKGROUND OF THE INVENTION

This invention relates to droplet flow cytometers such as are used to sort and analyze substances in both clinical and research applications. Specifically, the invention relates to components for such devices which control the differential charging of the droplets for deflection to sort them in the presence of an electrostatic field.

Droplet flow cytometers have been in clinical and research use for many years. Basically, the systems act to position small amounts of a substance within a sheath fluid. Through hydrodynamic focusing and laminar flow, the substance is split into individual cells and the like and is surrounded by the sheath fluid. This sheath fluid may be oscillated and allowed to exit a nozzle in a jet so as to regularly form droplets through the action of surface tension. Since the actual formation of the droplets takes some time after the sheath fluid exits the nozzle, the application of charge to individual droplets must be delayed from the actual time the substance exits the nozzle. This delay must be actually controlled so that when the droplets fall they may be deflected in an electrostatic field. Thus, in order to differentially charge individual droplets, very precise and uniform conditions are desirable within the jet. Unfortunately, variations exist. Thus, accurate processing requires not only properly ascertaining the appropriate time delay in the first place, but also periodically adapting to the changes practically experienced.

In establishing an appropriate droplet formation time delay estimate, two approaches seem to have been taken. The first is to utilize the theoretical predictions. While this approach represents an excellent first approximation, it has the significant shortcoming of not allowing for the variations which inherently exist in an operational system. Some adjustment remains necessary in order to adapt the theoretically predicted time delay to the actual time delay existing in a given system during a given run.

A second approach which appears to have been taken is that mentioned in related U.S. Pat. Nos. 4,317,520, 4,318, 480, 4,318,481, 4,318,482, 4,318,483, and 4,325,483. Although not the inventive subject of each of the references, each explains that those skilled in the art had set the time delay by utilizing a test sample which was sorted. The time delay was then manually adjusted until the expected number of target cells was achieved. Obviously, this approach does not take into consideration variations which exist when actually processing. Not only does it require interruption of the processing procedure, but it also ignores the fact that merely changing the substance from a test sample to an actual specimen can introduce changes (such as temperature changes, particulates, bubbles, and the like) which can significantly affect the delay time actually experienced for the formation of the droplets. It also requires manual intervention and thus makes the processing operation less automatic, more personnel intensive, and more susceptible to error.

As a result of the limitations which have appeared to exist in the prior efforts to ascertain a charging time delay, those skilled in the art have apparently been directed away from the aspect of properly setting the time delay and have instead pursued systems which are designed to control the uniformity of the jets so as to cause drop formation to occur at one location without any variation. This type of approach is demonstrated in the five related patents cited earlier as well as two other patents, related U.S. Pat. Nos. 4,487,320 and 4,691,829. As each of the references demonstrate, the approach those skilled in the art have generally taken is not to more accurately ascertain the appropriate time delay but rather to make that time delay as constant as possible. Thus, each of the references disclose feedback systems or monitoring systems which are designed to sense the location—not the time—at which droplet formation occurs. The system can then utilize that information as a feedback into the system to adjust that location to eliminate variations. While this type of approach may work well in some applications, it has a number of limitations. Significantly, these can include a failure to assure optimum drop delay timing in the first place. They also can be limited by the fact that the feedback systems themselves may act to move conditions within the flow cytometer away from optimum. As those skilled in the art readily understand, there are specific physical relationships which must exist for the flow cytometer to operate in an optimum fashion. The conditions should be set based upon the temperatures, pressures, frequencies, nozzle sizing, and the like for a given system. Any movement away from the correct relationships can negatively impact the resolution of the device. Thus, approaches which tend to apply corrections to counter the variations which may exist as a result of true conditions can represent an undesirable approach to solving the problem.

As mentioned, there has been a long felt and unsatisfied need for a device which not only automatically determines the optimum time delay for differential charging but also permits this time delay to be automatically ascertained during the actual processing of a substance. As the present invention shows, such a system is indeed possible and, in fact, can be implemented using arts and elements which have long been available. To some extent, apparently, solutions such as those of the present invention have not been achieved because those skilled in the art seem to have been directed away from the technical direction pursued in the present invention. This may have been the result of the fact that those skilled in the art did not truly appreciate the nature of the problem. It may also have been the result of the fact that those skilled in the art were misled by some of the presumptions and assumptions with respect to the types of systems which were appropriate for consideration. Although substantial attempts had been made at controlling a constant location for the formation of the drop, to some extent this may have only indicated that those skilled in the art failed to truly understand that the problem was not controlling the location but rather adapting to conditions as they may vary. The present invention shows that such an approach can be taken and that adapting to conditions actually experienced can be practically achieved. Until the present invention, a practical system which allowed for automatic determination of the exact time delay actually existing in the first place under true processing conditions was not available. Similarly, a practical system which has the ability to automatically ascertain the time delay and adapt to it during processing was not previously available.

SUMMARY OF THE INVENTION

The invention involves a variety of different designs which may be adapted depending upon the particular application involved. In a basic form, the system can involve components integrated with a traditional droplet flow cytometer so as to allow intermittent sampling during the processing operation. This sampling may be achieved automatically and may then be utilized in order to allow maximization of the substance processing through either manual or automatic adjustment of the charge delay timing. Through the use of an automatic sampler with a stepper motor and a movable platter, sample containers can be automatically positioned in the droplet free fall area. As each successive container is moved into place, a different time delay can be input to the system. Thus, through either manual or automatic analysis of the separate containers, the affect of each of these time delays can be ascertained so that the optimum time delay can be set or reset.

Accordingly, it is an object of the invention to provide an automatic design for more accurate initial setting of the drop formation time delay estimate. In keeping with this object it is the goal to ascertain an accurate initial setting in a repeatable and automatic fashion. A goal is thus to eliminate human error in some phases of the process. A goal is also to adapt an initial time delay setting to respond to variations and conditions as may be actually experienced. Similarly, a goal is to avoid undue reliance on theoretical predictions and instead to establish conditions based upon actual conditions.

Another object of the invention is to allow for a system which can be used during processing without a substantial interruption of that processing. Thus a goal is to provide a system which operates rapidly with minimum need for operator involvement. Obviously, a completely automatic system is a goal as well, however, a goal is also to avoid unnecessary complication and expense. Thus, a goal is to provide a system which may be adapted and utilized in fully automatic or some combination of automatic and manual modes.

Yet another object of the invention is to avoid settings in the system which are suboptimal. In keeping with this object, a goal is to avoid theoretical predictions and to instead rely upon conditions actually experienced to the extent possible. Similarly, a goal is to set the system based solely upon conditions experienced with no reliance upon other factors which may or may not exist. In order to achieve the most optimal setting while utilizing an actual substance run, a goal is to quickly accomplish sampling over a variety of delays so that actual variations in the substance are minimized or eliminated.

Naturally, further objects of the invention are disclosed throughout other areas of the specification and claims.

DETAILED DESCRIPTION OF THE PREFERRED EMBODIMENT

Figure 1:
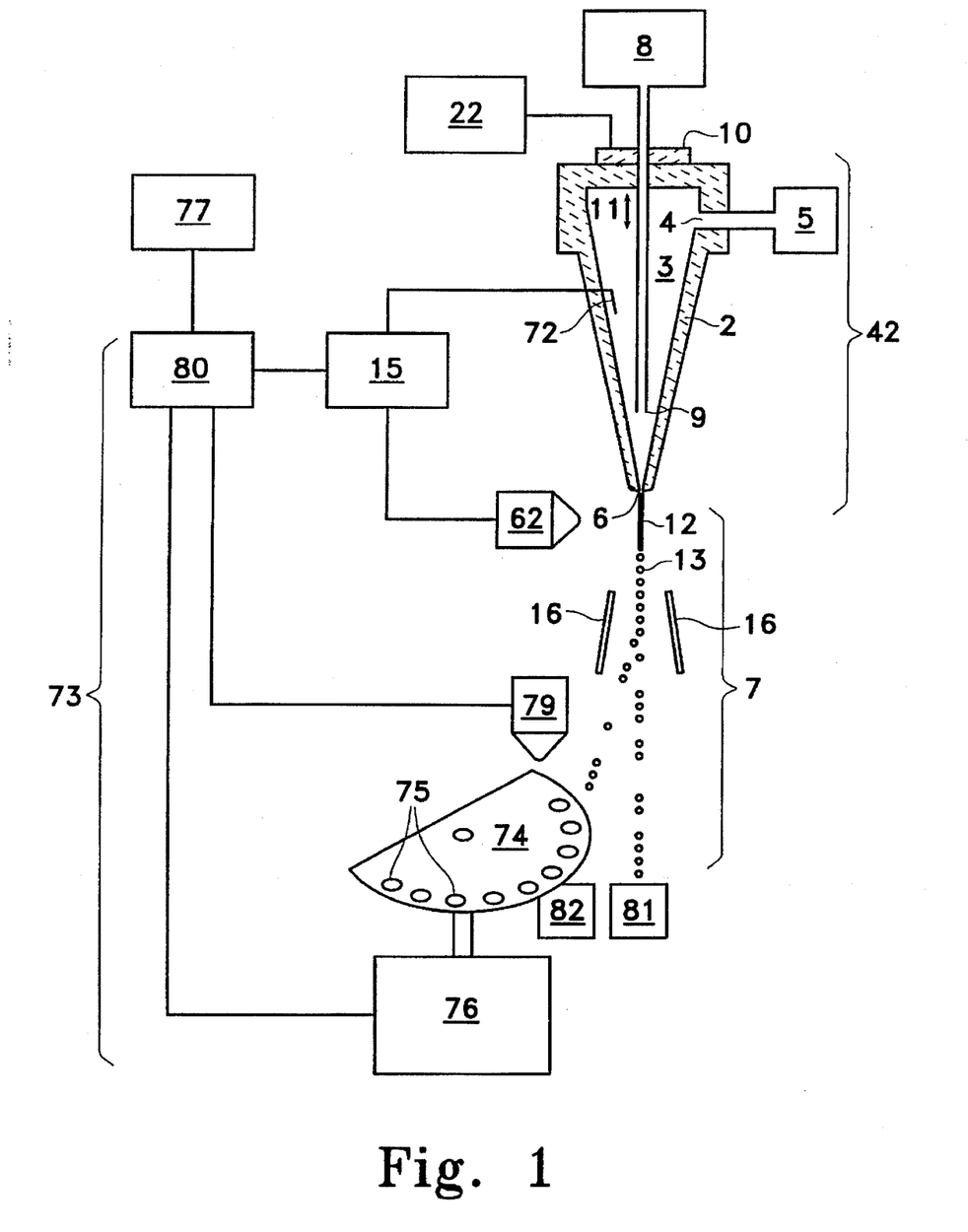
FIG. 1 is a schematic view of the system which senses droplet formation time delay according to the present invention.

The present invention involves different techniques which may be implemented in a variety of ways. As mentioned, these implementations may be adapted as appropriate to specific applications and may involve a combination of manual and automatic features. FIG. 1 shows a droplet flow cytometer which has an automatic droplet sampler (73) integrated into it. As those skilled in the art well understand, the droplet flow cytometer includes a nozzle system (42). Nozzle system (42) includes nozzle container (2) which establishes nozzle volume (3). Nozzle volume (3) has introduced within it a flow of a sheath fluid from sheath reservoir (5) through sheath fluid port (4). Some substance to be analyzed can then be introduced within the sheath fluid inside nozzle volume (3) from substance reservoir (8) through substance introduction port (9).

In order to form regular droplets, an oscillator (10) may be adapted to cause oscillations which cause pressure waves within or actual movement of the sheath fluid. Oscillator (10) may be controlled by alternating voltage source (22) so that the oscillations may be accurately controlled. In this fashion, the sheath fluid responds to oscillator (10). The sheath fluid, together with its entrained substance can then be hydrodynamically focused so that single cells and the like may be emitted from nozzle exit (6) into free fall area (7) below. By allowing the sheath fluid to exit from nozzle volume (3), jet (12) is created. This jet occurs within free fall area (7) where it may be analyzed or further processed.

As a result of oscillations within the sheath fluid, jet (12) is regularly varied so that through the action of surface tension, droplets (13) are formed from the sheath fluid. Each of the droplets (13) may be differentially characterized through an analysis of them or jet (12) prior to droplet formation to assess whether they contain a particular item or type of substance. This may involve analyzing individual cells or cell fragments. Often this is accomplished through analysis of jet (12) by a same substance property sensor (62).

As may be appreciated from FIG. 1, droplets (13) do not immediately form at nozzle exit (6). Some delay occurs based upon the time it takes surface tension to act to cause droplets (13). This droplet formation time delay can vary for actual processing conditions as mentioned earlier.

Importantly, many droplet flow cytometers act to sense a specific property of the substance being analyzed. This can occur within free fall area (7). As shown in FIG. 1, substance property sensor (62) may be positioned so that it senses emissions occurring from the substance within jet (12). The signals sensed by substance property sensor (62) may be utilized by analysis equipment (15) in a host of different ways depending upon the particular substance or application involved. While natural emissions may be utilized for analysis, it is frequently common to cause fluorescence of the substance and then to analyze these emissions. This may be created by stimulating the substance after it exits from nozzle container (2) through some type of substance stimulation source such as a laser. This laser may then cause the substance to fluoresce. The fluorescence emissions may then be sensed by substance property sensor (62). Naturally, in keeping with the broad nature of the invention, it should be understood that substance property sensor (62), and indeed the property being sensed, should not be limited to only fluorescence emissions. All that is necessary is that some distinguishing feature be determined in order to allow discrimination between droplets (13).

As those involved with droplet flow cytometers for sorting applications well understand, droplets (13) created may then be characterized by components including sorting equipment (16). As shown, sorting equipment (16) creates an electrostatic field so that charged droplets are deflected whereas uncharged droplets are not. The differential charging of one droplet as opposed to another may be achieved through the interconnection of analysis equipment (15) with electrode (72). Since analysis equipment (15) can obtain its information from substance property sensor (62), electrode (72) can be responsive to substance property sensor (62). Electrode (72) may be positioned within nozzle volume (3) so as to cause a charge on the sheath fluid. Thus, the sheath fluid is responsive to electrode (72). The charge may be transmitted to the end of jet (12) so that at the instant when a droplet is formed, that droplet may be charged. Electrode (72) may then be quickly neutralized so that the next droplet formed does not contain a charge. In this fashion when droplets (13) pass through sorting equipment (16) some individual droplets—namely those which do or do not contain the desired substance as determined by analysis equipment (15)—will be deflected. The deflected droplet can thus be collected in sample collection container (82) whereas the undeflected droplets can pass to drain on receptacle (81). The appropriate timing of the charging of jet (12) through action of electrode (72) requires the accurate utilization of a droplet formation time delay estimate such as the amount of time it takes for the droplet to form after substance property sensor (62) and analysis equipment (15) have actually determined whether or not a particular location in jet (12) contains the desired substance.

As shown in FIG. 1, the preferred embodiment includes automatic droplet sampler (73). This may be configured so as to act to sample the droplets sorted by sorting equipment (16). Naturally, a host of different designs are intended to be included within the meaning of term "automatic droplet sampler" ranging from devices as those shown which physically sample to those which simply involve sensors or the like. In the presently preferred embodiment physical sampling is utilized with manual testing. Thus, as shown automatic droplet sampler (73) has a plurality of collection areas or containers (75) situated on or supported by movable platter (74). Through moving movable platter (74), different containers (75) may be sequentially positioned in free fall area (7) and thus may gather droplets. Importantly, movable platter (74) may be responsive to stepper (76) so that the various containers (75) may be separately and incrementally positioned in free fall area (7). Thus, throughout one single sampling event, a number of different samples may be taken.

By including a droplet formation time delay adjustment (80) in a fashion which is coordinated with automatic droplet sampler (73), optimization of the time delay can be achieved. This may be achieved by creating some automatic substance maximization means—essentially, any component, software, or circuitry which automatically provides information to allow maximization of the substance sorted. This substance maximization means may include increment control (77), a device which acts to automatically adjust the various time delays actually applied by analysis equipment (15) in controlling electrode (72). Through increment control (77), the time delay applied by analysis equipment (15) to electrode (72) may be varied in incremental amount as each different container (75) is positioned within free fall area (7). Thus, each container (75) can represent a different time delay amount. These results can then be used to achieve an optimum (or more optimum) drop formation time delay estimate.

In an automated configuration, some type of cell counter (79) ranging from a scale for weight determination, to a height measurement for volume determination, to any other type of sensing device) may be included. This cell counter (79) may yield information which allows time delay adjustment (80) to alter the actual time delay used during processing. In this fashion, different time delay amounts may be applied and tested automatically (if such complexity is warranted) to see which yields the maximum count. To accomplish this, it can be seen that the delay adjustment (80) is connected so that movable platter (74) and it are responsive to each other or at least coordinated with each other. Thus, automatic droplet sampler (73) and the time delay adjustment are also coordinated. The one which does yield the maximum count can then be utilized to adjust the droplet formation time delay estimate utilized by analysis equipment (15) and thus more optimally set the device.

As may be easily appreciated, different configurations are possible using the basic teachings of the invention. With respect to droplet sampler (73), not only may other configurations be achieved but also even the configuration such as that involving movable platter (74) and stepper (76) may be controlled in different ways. These range from manually controlled sampling, to an interconnection with some type of operator control, to a fully automatic control. In either configuration, automatic droplet sampler (73) may be configured to intermittently sample the substance actually processed while accomplishing the analysis of that substance. Thus, even though some substance may be removed by automatic droplet sampler (73) when it utilizes separate containers (as opposed to merely a sensor), the analysis is considered uninterrupted since no changes in the substance or flows are made as a result of the sampling step. Similarly, repetitive testing can occur through the use of more than one container (75) on movable platter (74). These repetitive tests can then be used to adjust the droplet formation time delay estimate without interrupting the analysis or processing step. Naturally, this sampling could occur only at an initialization routine or may regularly occur throughout processing.

Similarly, a variety of different configurations with respect to the control of the time delay are possible. Again, it may be set manually or automatically. In the preferred embodiment an initial setting may be manually achieved. When sampling is desired, this sampling may be triggered. This may cause the initial droplet formation delay estimate to be reduced by some amount to establish a lower droplet formation time delay estimate. This amount may be a multiple of an incremental amount initially established through incremental control (77). In the preferred embodiment, this is automatically achieved by reducing the initial drop formation time delay estimate by an integer multiple of the initially set incremental amount which is half the number of sample container (75) provided. In so doing, the initial drop formation time delay estimate is bracketed. After positioning the first container (75) so as to gather droplets (13) for a set amount of time, stepper (76) may be operated to move to the next container (75). Simultaneously, time delay adjustment (80) can then increment the lower droplet formation time delay estimate so established. Successive integer multiples of the incremental amount may then be added to the lower limit droplet formation time delay estimate for each successive container (75). This repetitive adding of increased multiples can step the time delay through a sequence which allows for sampling corresponding to a variety of different time delay estimates. Thus, time delay adjustment (80) is coordinated with automatic droplet sampler (73) to assess the effect of different time delays by sampling droplets which have been subjected to different differential charging times. By using a plurality of containers (75) and altering the droplet formation time delay estimate and then again sampling the droplets, the effect at different times can be practically ascertained for any given system.

As may be appreciated and in keeping with one of the goals of the invention, this entire processing step, can be achieved rapidly. Thus, the alteration of the droplet formation time delay estimates and the movement of container (75) may be accomplished automatically in times as short as a second or less. Since it is unlikely that the substance varies in such a short time frame, maximization of the count can be achieved with sufficient confidence to reset the droplet formation delay estimate utilized by analysis equipment (15). This aids in permitting the actual processing substance to replace a need for a separate test substance.

In general, it is also possible to utilize the system to establish an appropriate time delay with increasing accuracies. In a situation in which a maximum is identified as existing within a range of time delays tested in any sampling event—that is, a single run of movable platter (74) achieving a number of different samples—an increasing degree of accuracy can then be automatically applied. To do this, increment control (77) may be operated to create a reduced incremental amount and the entire process may be reinitiated (manually or automatically) utilizing the revised drop delay formation time estimate as the starting point. When this occurs, the range of drop delay time estimates tested can be reduced so that a revised lower limit droplet formation time delay estimate is used. This revised lower limit droplet formation time delay estimate may then have added to it increasing integer multiples of the reduced incremental amount as each sample container is repositioned in free fall area (7). Further, in any sampling conducted, it should be understood that not only integer multiples are possible but also noninteger multiples. Also, values may be based upon expected performance or may simply allow for more accuracy near the center of the range tested. Using the reduced incremental amount, the entire process can be reinstituted to more accurately establish the appropriate droplet formation time delay estimate. Further, in instances in which no maximum is identified in a particular run, the trend may be analyzed so as to allow a further adjustment (including an increase in the incremental amount, if desired) and the processing can either occur at either the top or bottom of the time delay estimate range tested or at some other value. This may continue until a maximum is identified. This aspect alone represents an improvement over the prior art in that even the initial setting of the first droplet formation time delay estimate can be accomplished automatically without any need for prior knowledge of the system.

Figure 2:
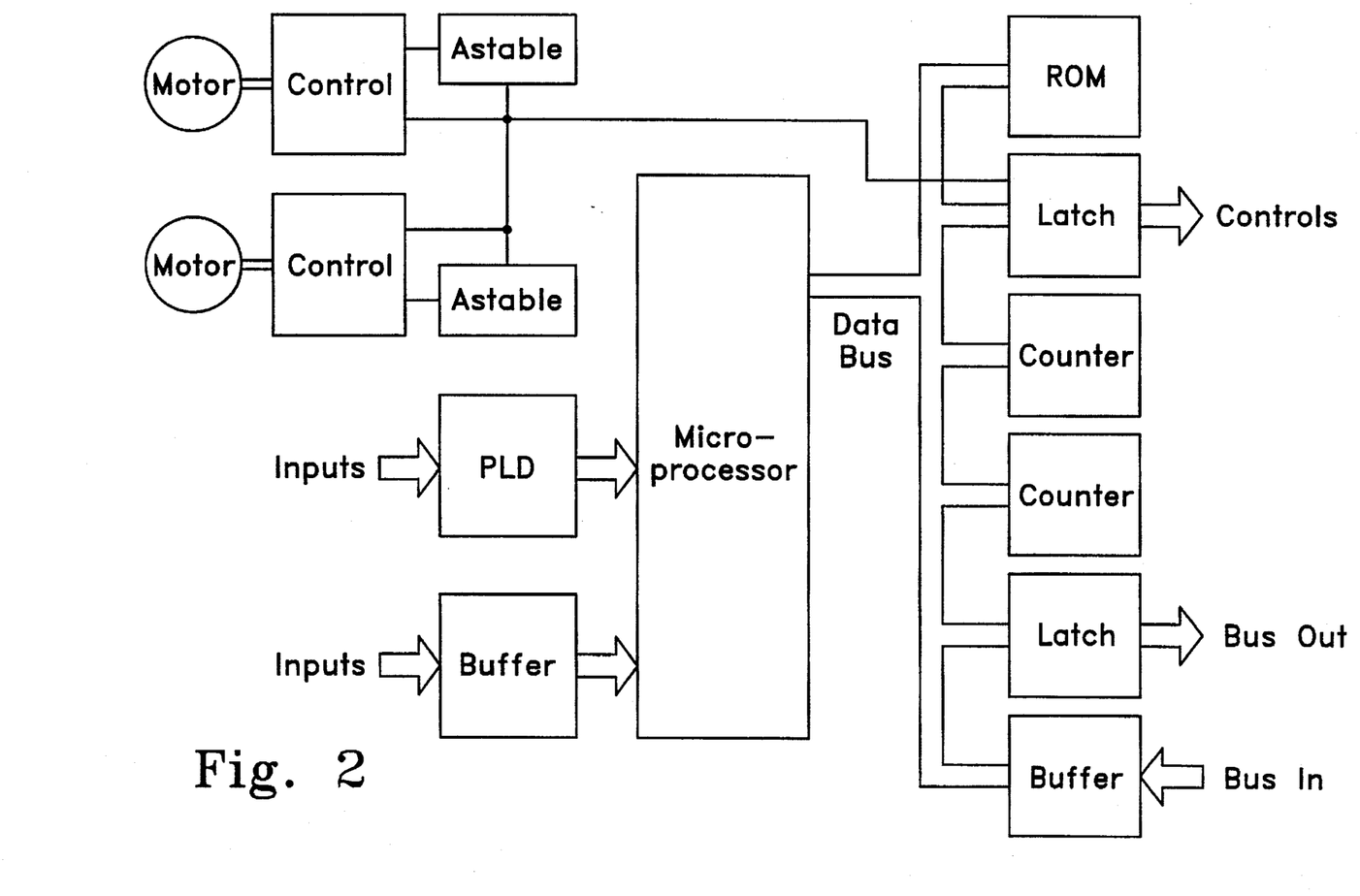
FIG. 2 is a block diagram of a circuit design which can be used to control the automatic sampling functions.

As mentioned earlier, a variety of different configurations are possible. This may include hardware or software embodiments. As shown in FIG. 2, a combination of hardware and software connections are preferred. Through such an arrangement, software can be written and provided to a microprocessor so that specific control may be easily achieved. Since the basic operation can be easily understood these subroutines and the like can be easily achieved by those skilled in the art. To further explain the hardware arrangement used in the preferred embodiment (which combines manual and automatic features), FIG. 2 shows one possible configuration of components to serve as automatic droplet sampler (73).

As shown in FIG. 2, this circuitry is a microprocessor based system. As could be easily understood, through several types of inputs the microprocessor can be controlled by the operator to select a particular mode of operation as well as to store information for use when the automatic sampling is commenced. Further, the user can configure switches to serve as data inputs to this system. These switches may be front panel switches on a flow cytometer that allow the user to input a selected program or to select the property or condition that controls the stepper motor. To facilitate these varied functions, as shown in FIG. 2 some of the inputs may be fed to the microprocessor by using a programmable logic device (PLD) while others may be buffered to the microprocessor.

In the preferred embodiment an 8031 family microprocessor is used. For this type of device some of the inputs can be configured to serve as the microprocessor's counter. Specifically, one port (such as Port 3) of the microprocessor may be used to allow the user to configure some of the data inputs as either external interrupts or timer/counter inputs. These can thus act to vary the time delay increment amount. Further, the microprocessor based system may utilize either an internal or an external memory for program storage. Due to the type of design selected, an external ROM memory is used in the design shown.

To control the sampling event, the microprocessor is configured or programmed to process the input data and to output control signals to the data bus, as shown in FIG. 2. These control signals can be latched so that they can be used as output control signals. These control signals can act to operate one or more stepper motors. (The second stepper motor shown in FIG. 2 is not used in this embodiment.) As mentioned, the stepper can position a movable platter to sequentially different positions while simultaneously adjusting a time delay control. Thus containers on the movable platter can be positioned to catch droplets from the flow cytometer which correspond to different time delay values.

To adjust the automatic droplet sampler elements, the number of time delay settings that the user selects may be input. Alternatively, the microprocessor programming may be configured to make this determination. In operation the microprocessor can act to step the stepper motor (and, consequently, the movable platter or other element) through an equivalent number of positions. This allows the platter containers to gather samples at each successive time delay setting for an optimum time delay setting to be determined.

To accomplish the task of stepping the system through the various time delay settings, the microprocessor loads a counter with the number of steps appropriate to the distance between the containers. Then the time delay settings can be gated to an oscillator (labelled "Astable" in FIG. 2). The oscillator can be configured to provide a constant time period for each container on the movable platter to be positioned to catch droplets from the flow cytometer. By keeping this time period constant for each step by the stepper motor, the number of droplets caught by each container can be more easily compared.

Finally, the microprocessor based system can communicate with an external computer through a traditional interface. This interface (often referred to as a GPIO interface) can be interrupt driven. On receiving an interrupt from the external computer, the microprocessor can then acknowledge the interrupt and input data from the external computer that was latched by the GPIO interface.

Importantly, it should be understood that the configuration shown in FIG. 2 is only one of a great variety of designs possible. Thus, none of the arrangements suggested should be considered to limit the scope of designs intended to fall within the scope of this invention. While only one preferred design is used at present, alternative processors, analog circuitry, and very different programming are all intended to be encompassed. The design shown is simply presented to facilitate an understanding of the invention, not to limit it.

The foregoing discussion and the claims which follow describe the preferred embodiment of the present invention. Particularly with respect to the claims, it should be understood that changes may be made without departing from its essence. In this regard, it is intended that such changes would still fall within the scope of this patent. It simply is not practical to describe and claim all possible revisions which may be accomplished. To the extent such revisions utilize the essence of the invention, each should naturally be understood to fall within the breadth of protection encompassed by this patent. This is particularly true for the present invention since its concepts are relatively basic and fundamental in nature and may be broadly applied in a variety of ways depending upon the type of application or system involved, the degree of automation desired, or a variety of other factors.

We claim:

1. A method of droplet flow cytometry which senses droplet formation time delay comprising the steps of:

a. establishing a nozzle volume;
 b. introducing a flow of sheath fluid into said nozzle volume;
 c. introducing a flow of a substance within said sheath fluid in said nozzle volume;
 d. establishing an oscillation to which said sheath fluid is responsive;
 e. allowing said sheath fluid to exit from said nozzle volume;
 f. analyzing a property of said substance entrained within said sheath fluid;
 g. forming a plurality of droplets from said sheath fluid after allowing said sheath fluid to exit from said nozzle volume;
 h. creating a droplet formation time delay estimate;
 i. differentially charging some individual droplets based upon the step of analyzing a property of said substance and said droplet formation time delay estimate;
 j. intermittently sampling said droplets while accomplishing the step of analyzing a property of said substance; and
 k. analyzing said intermittent sampling;
 l. adjusting said droplet formation time delay estimate based upon the step of analyzing said intermittent sampling.

2. A method of droplet flow cytometry which senses droplet formation time delay as described in claim 1 wherein said droplets sampled contain said substance and further comprising the steps of:

a. ascertaining a time delay amount which yields a maximum count of said substance; and
 b. adjusting said droplet formation time delay estimate to said time delay amount which yields a maximum count of said substance.

3. A method of droplet flow cytometry which senses droplet formation time delay as described in claim 2 wherein the step of intermittently sampling said droplets while accomplishing the step of analyzing a property of said substance comprises the step of repetitively testing droplets which have been subjected to said step of differentially charging.

4. A method of droplet flow cytometry which senses droplet formation time delay as described in claim 3 wherein the step of repetitively testing droplets which have been subjected to said step of differentially charging comprises the steps of:

a. sampling said droplets a first time;
 b. altering said droplet formation time delay estimate; and then
 c. sampling said droplets a second time.

5. A method of droplet flow cytometry which senses droplet formation time delay as described in claim 4 wherein the steps of sampling said droplets, altering said droplet formation time delay estimate, and again sampling said droplets are each accomplished automatically.

6. A method of droplet flow cytometry which senses droplet formation time delay as described in claim 5 wherein the step of altering said droplet formation time delay estimate comprises the step of establishing a incremental amount by which to change said droplet formation time delay estimate.

7. A method of droplet flow cytometry which senses droplet formation time delay as described in claim 6 wherein the step of altering said droplet formation time delay estimate further comprises the steps of:

a. reducing said droplet formation time delay estimate by a multiple of said incremental amount to establish a lower limit droplet formation time delay estimate; and then
 b. repetitively adding increased multiples of said incremental amount to said lower limit droplet formation time delay estimate.

8. A method of droplet flow cytometry which senses droplet formation time delay as described in claim 7 wherein the step of altering said droplet formation time delay estimate further comprises the steps of:

a. creating a reduced incremental amount by which to change said droplet formation time delay estimate;
 b. reducing said droplet formation time delay estimate by a multiple of said reduced incremental amount to establish a revised lower limit droplet formation time delay estimate; and then
 c. repetitively adding increased multiples of said reduced incremental amount to said revised limit droplet formation time delay estimate.

9. A droplet flow cytometer system which senses droplet formation time delay comprising:

a. a nozzle container establishing a nozzle volume and having a nozzle exit;
 b. a sheath fluid port located within said nozzle volume;
 c. a substance introduction port located within said nozzle volume;
 d. an oscillator to which said sheath fluid is responsive;
 e. a free fall area below said nozzle exit and within which said droplet forms with some droplet formation time delay;
 f. a substance property sensor responsive to said free fall area;
 g. an electrode to which said sheath fluid is responsive and which is responsive to said substance property sensor; and
 h. an automatic substance maximization means to which said electrode is responsive which conducts intermittent analysis and which adjusts said droplet formation time delay based upon said intermittent analysis.

10. A droplet flow cytometer system which senses droplet formation time delay as described in claim 9 wherein said substance maximization means comprises:

a. an automatic droplet sampler which samples said droplets; and
 b. a cell counter which is responsive to said automatic droplet sampler.

11. A droplet flow cytometer system which senses droplet formation time delay as described in claim 10 wherein said substance maximization means further comprises a time delay adjustment which is coordinated with said automatic droplet sampler.

12. A droplet flow cytometer system which senses droplet formation time delay comprising:

a. a nozzle container establishing a nozzle volume and having a nozzle exit;

b. a sheath fluid port located within said nozzle volume;

c. a substance introduction port located within said nozzle volume;

d. an oscillator to which said sheath fluid is responsive;

e. a free fall area below said nozzle exit and within which said droplet forms;

f. a substance property sensor responsive to said free fall area;

g. an electrode to which said sheath fluid is responsive and which is responsive to said substance property sensor; and h. an automatic droplet sampler which intermittently samples said droplets;

i. an analysis system which is responsive to said automatic droplet sampler; and j. a droplet formation time delay adjustment which is coordinated with said analysis system.

13. A droplet flow cytometer system which senses droplet formation time delay as described in claim 12, or 11 wherein said automatic droplet sampler comprises:

a. a movable platter positioned so at to move into said free fall area; and b. a plurality of containers on said movable platter.

14. A droplet flow cytometer system which senses droplet formation time delay as described in claim 13 wherein said automatic droplet sampler further comprises a stepper wherein said movable platter is responsive to said stepper.

15. A droplet flow cytometer system which senses droplet formation time delay as described in claim 13 wherein said droplet formation time delay adjustment is coordinated with said movable platter.

16. A droplet flow cytometer system which senses droplet formation time delay as described in claim 15 wherein said automatic droplet sampler further comprises an increment control to which said droplet formation time delay adjustment and said movable platter are responsive.

17. A droplet flow cytometer system which senses droplet formation time delay as described in claim 16 wherein said increment control is adjustable.

* * * * *

UNITED STATES PATENT AND TRADEMARK OFFICE
CERTIFICATE OF CORRECTION

PATENT NO. : 5,643,796
DATED : July 1, 1997
INVENTOR(S) : Ger Van den Engh and Richard J. Esposito It is certified that error appears in the above-indentified patent and that said Letters Patent is hereby corrected as shown below:

Column 1, after the title, "System for Sensing Droplet Formation Time Delay in a Flow Cytometer", insert --The U.S. Government has a paid-up license in this invention and the right in limited circumstances to require the patent owner to license others on reasonable terms as provided for by the terms of a contract number DE-FG06-93ER-61662 awarded by the Department of Energy.--

Signed and Sealed this

Fifteenth Day of May, 2001

Attest:

NICHOLAS P. GODICI

Attesting Officer  Acting Director of the United States Patent and Trademark Office